(12) United States Patent
Benabdillah

(10) Patent No.: US 7,740,664 B2
(45) Date of Patent: Jun. 22, 2010

(54) COMPOSITION COMPRISING AT LEAST ONE SILICONE COMPOUND AND AT LEAST ONE ORGANOSILANE

(75) Inventor: Katarina Benabdillah, Le Plessis-Bouchard (FR)

(73) Assignee: L'oreal S.A., Paris (FR)

( * ) Notice: Subject to any disclaimer, the term of this patent is extended or adjusted under 35 U.S.C. 154(b) by 156 days.

(21) Appl. No.: 12/003,125

(22) Filed: Dec. 20, 2007

(65) Prior Publication Data

US 2009/0183320 A1 Jul. 23, 2009

Related U.S. Application Data

(60) Provisional application No. 60/898,746, filed on Feb. 1, 2007.

(30) Foreign Application Priority Data

Dec. 20, 2006 (FR) .................................. 06 55753

(51) Int. Cl.
*A61Q 5/10* (2006.01)
*A61Q 5/12* (2006.01)

(52) U.S. Cl. ........................ 8/405; 8/431; 8/581; 8/632; 8/127.51; 8/128.3; 424/70.12

(58) Field of Classification Search ............... 8/405, 8/431, 581, 632, 127.51, 128.3; 424/70.12
See application file for complete search history.

(56) References Cited

U.S. PATENT DOCUMENTS

| | | | |
|---|---|---|---|
| 2,643,375 A | 6/1953 | Gant | |
| 2,782,790 A | 2/1957 | Hersh et al. | |
| 2,787,274 A | 4/1957 | Gant et al. | |
| 2,840,087 A | 6/1958 | Hersh | |
| 3,175,993 A | 3/1965 | Weyenberg et al. | |
| 4,344,763 A * | 8/1982 | Tolgyesi et al. | 8/127.51 |
| 4,772,675 A | 9/1988 | Kiosowski et al. | |
| 4,871,827 A | 10/1989 | Kiosowski et al. | |
| 4,888,380 A | 12/1989 | Kamis et al. | |
| 4,898,910 A | 2/1990 | Kamis et al. | |
| 4,902,499 A | 2/1990 | Bolich, Jr. et al. | |
| 4,906,719 A | 3/1990 | Chu et al. | |
| 4,962,174 A | 10/1990 | Bilgrien et al. | |
| 5,362,486 A | 11/1994 | Nandagiri et al. | |
| 5,811,085 A | 9/1998 | Halloran | |
| 5,968,286 A | 10/1999 | Crudele et al. | |
| 6,165,971 A | 12/2000 | Oppenlander et al. | |
| 6,368,581 B1 | 4/2002 | Karlen et al. | |
| 6,432,386 B1 | 8/2002 | Rollat-Corvol et al. | |
| 6,752,984 B2 | 6/2004 | Butts et al. | |
| 7,217,296 B2 | 5/2007 | Pastore et al. | |
| 7,261,744 B2 | 8/2007 | Gourlaouen et al. | |
| 7,303,589 B2 | 12/2007 | Greaves et al. | |
| 2001/0004654 A1 | 6/2001 | Sugimoto et al. | |
| 2002/0076424 A1 | 6/2002 | Birkel et al. | |
| 2002/0155082 A1 | 10/2002 | Richard et al. | |
| 2003/0152543 A1 | 8/2003 | Legrand et al. | |
| 2003/0203978 A1 | 10/2003 | O'Brien et al. | |
| 2004/0052745 A1 | 3/2004 | Bernard et al. | |
| 2005/0011018 A1 | 1/2005 | Greaves et al. | |
| 2005/0028301 A1 | 2/2005 | Pastore | |
| 2005/0232882 A1 | 10/2005 | Bebot et al. | |
| 2006/0010617 A1 | 1/2006 | Gourlaouen et al. | |
| 2006/0031999 A1 | 2/2006 | De Boni et al. | |
| 2006/0045862 A1 | 3/2006 | Tada et al. | |
| 2006/0110351 A1 | 5/2006 | Koehler et al. | |
| 2007/0274941 A9 | 11/2007 | Blin | |
| 2008/0184496 A1 | 8/2008 | Brun et al. | |
| 2008/0233158 A1 | 9/2008 | Blin et al. | |
| 2008/0289647 A1 | 11/2008 | Genain | |
| 2008/0292573 A1 | 11/2008 | Giroud | |
| 2009/0183320 A1 | 7/2009 | Benabdillah | |

FOREIGN PATENT DOCUMENTS

| | | |
|---|---|---|
| DE | 200 05 808 | 8/2000 |
| EP | 0 159 628 | 10/1985 |
| EP | 0 465 744 | 1/1992 |
| EP | 0 473 039 | 3/1992 |
| EP | 0 865 787 | 9/1998 |
| EP | 0 958 804 | 11/1999 |
| EP | 0 959 066 | 11/1999 |
| EP | 1 101 486 | 5/2001 |
| EP | 1 101 487 | 5/2001 |
| EP | 1 175 893 | 1/2002 |
| EP | 1 190 699 | 3/2002 |
| EP | 1 312 352 | 5/2003 |
| EP | 1 426 027 | 6/2004 |
| EP | 1 433 459 | 6/2004 |
| EP | 1 582 198 | 10/2005 |
| EP | 1 616 558 | 1/2006 |

(Continued)

OTHER PUBLICATIONS

STIC Search Report for U.S. Appl. No. 12/004,051 dated Aug. 18, 2008.*

(Continued)

*Primary Examiner*—Eisa B Elhilo
(74) *Attorney, Agent, or Firm*—Finnegan, Henderson, Farabow, Garrett & Dunner LLP

(57) ABSTRACT

The present disclosure provides a composition for treating keratin fibers, for example, human keratin fibers such as the hair. The present disclosure provides a composition for dyeing keratin fibers, comprising: at least one compound X and at least one compound Y, wherein at least one of the compounds X and Y is a silicone compound, wherein when X and Y are placed in contact with each other they react together via a hydrosilyation reaction, a condensation reaction, or a crosslinking reaction in the presence of at least one peroxide; and at least one alkoxysilane comprising a single silicon atom.

32 Claims, No Drawings

FOREIGN PATENT DOCUMENTS

| | | |
|---|---|---|
| EP | 1 938 865 | 7/2008 |
| EP | 1 941 930 | 7/2008 |
| FR | 2 746 102 | 9/1997 |
| FR | 2 760 971 | 9/1998 |
| FR | 2 811 546 | 1/2002 |
| FR | 2 830 189 | 4/2003 |
| FR | 2 851 464 | 8/2004 |
| FR | 2 874 178 | 2/2006 |
| GB | 2 186 890 | 8/1987 |
| GB | 2 401 316 | 11/2004 |
| GB | 2 407 496 | 5/2005 |
| JP | 11-349450 | 12/1999 |
| WO | WO 93/17060 | 9/1993 |
| WO | WO 96/12754 | 5/1996 |
| WO | WO 97/17057 | 5/1997 |
| WO | WO 98/44906 | 10/1998 |
| WO | WO 99/13843 | 3/1999 |
| WO | WO 99/13846 | 3/1999 |
| WO | WO 01/14458 | 3/2001 |
| WO | WO 01/96450 | 12/2001 |
| WO | WO 02/067877 | 9/2002 |
| WO | WO 2004/012691 | 2/2004 |
| WO | WO 2004/084847 | 10/2004 |
| WO | WO 2004/091473 | 10/2004 |
| WO | WO 2005/000856 | 1/2005 |
| WO | WO 2006/028612 | 3/2006 |
| WO | WO 2007/071706 | 6/2007 |
| WO | WO 2007/071885 | 6/2007 |
| WO | WO 2007/071886 | 6/2007 |

OTHER PUBLICATIONS

French Search Report for FR 06/55753, dated Jul. 18, 2007.
Copending U.S. Appl. No. 12/000,886, filed Dec. 18, 2007.
Copending U.S. Appl. No. 12/003,067, filed Dec. 19, 2007.
Copending U.S. Appl. No. 12/003,093, filed Dec. 20, 2007.
Copending U.S. Appl. No. 12/004,051, filed Dec. 20, 2007.
Copending U.S. Appl. No. 12/004,057, filed Dec. 20, 2007.
Copending U.S. Appl. No. 12/004,072, filed Dec. 20, 2007.
Copending U.S. Appl. No. 12/004,103, filed Dec. 20, 2007.
Copending U.S. Appl. No. 12/086,758, filed Jun. 19, 2008.
Copending U.S. Appl. No. 12/097,978, filed Feb. 13, 2009.
English language Abstract of FR 2 760 971, dated Sep. 25, 1998.
English language Abstract of JP 11-349450, dated Dec. 21, 1999.
English language Abstract of WO 2007/071885, dated Jun. 28, 2007.
English language Abstract of WO 2007/071886, dated Jun. 28, 2007.
European Search Report for EP 07 12 3272, dated Jul. 15, 2008.
European Search Report for EP 07 12 3273, dated Nov. 11, 2009.
French Search Report for FR 06/55719, dated Aug. 21, 2007.
French Search Report for FR 06/55726, dated Aug. 8, 2007.
French Search Report for FR 06/55728, dated Oct. 19, 2007.
French Search Report for FR 06/55732, dated Sep. 11, 2007.
French Search Report for FR 06/55754, dated Jul. 18, 2007.
French Search Report for FR 06/55755, dated Aug. 1, 2007.
French Search Report for FR 06/55756, dated Aug. 1, 2007.
International Search Report for PCT/EP2006/069973, dated Jul. 10, 2007.
International Search Report for PCT/FR2006/051399, dated Jul. 16, 2007.
Kim, et al., "Selective Topochemical Photoreaction of Crystallized 2,3-Bis(2-phenylethenyl)-4,5-dicyanopyrazines," Chemistry Letters, (1999), (2), pp. 143-144.
Kishi, et al., "Development and Application of Latent Hydrosilylation Catalyst [6]: Control of Activity of Platinum Catalyst by Isocyanide Derivatives on the Crosslinking of Silicone Resin via Hydrosilylation," Internation Journal of Adhesion & Adhesives, 20, (2000), pp. 253-256.
Kusakabe, M. et al., "Review of Innovative Developments of Silyl-Modified Polymers for Sealant, Adhesive and Coating Applications," European Coating, 12-B, (2005), pp. 43-49.
Meylan, et al., "Atom/Fragment Contribution Method for Estimating Octanol-Water Partition Coefficients," Journal of Pharmaceutical Sciences, vol. 84, No. 1, Jan. 1995, pp. 83-92.
Office Action mailed Jun. 11, 2009, in co-pending U.S. Appl. No. 12/000,886.
Probster, M., "Dichstoffe mit silanvernetzenden Polymeren: Trends und Perspektiven," Adhesion-Kleben & Dichten, (2004), 481 (1-2), pp. 12-14.
Schwander, H. et al., "Fluorescent Dyes," Ullman's Encyclopedia of Industrial Chemistry Release 2005, 7th Edition, pp. 1-14.
Tomalia, D. et al., "Starburst Dendrimers: Molecular Level Control of Size, Shape, Surface Chemistry, Topology, and Flexibility from Atoms to Macroscopic Matter," Angew. Chem. Int. Ed. Engl., vol. 29, No. 2, (1990), pp. 138-175.

* cited by examiner

COMPOSITION COMPRISING AT LEAST ONE SILICONE COMPOUND AND AT LEAST ONE ORGANOSILANE

This application claims benefit of U.S. Provisional Application No. 60/898,746, filed Feb. 1, 2007, the contents of which are incorporated herein by reference. This application also claims benefit of priority under 35 U.S.C. §119 to French Patent Application No. FR 06 55753, filed Dec. 20, 2006, the contents of which are also incorporated herein by reference.

The present disclosure provides a composition for treating keratin fibers and, for instance, human keratin fibers such as the hair.

The hair is generally damaged and weakened by the action of external atmospheric agents such as light and weather, and by mechanical or chemical treatments such as brushing, combing, bleaching, perming and/or dyeing. The result is that the hair is often difficult to manage: for example, it may be difficult to disentangle or to style, and the hair, even when lush, may be difficult to retain a good-looking style, owing to the fact that the hair lacks vigor, volume, and verve.

To remedy this situation, therefore, it is now common to use styling products which allow the hair to be conditioned, providing the hair with, for instance, body, mass, sheen or volume. These styling products are generally cosmetic hair care compositions which comprise at least one polymer that has affinity for the hair and which most commonly has the function of forming a film on the surface of the hair, with the aim of modifying its surface properties, in order to condition the hair, for example. In order to obtain such an effect, it is common practice to use polysiloxanes, for example those described in French Patent Nos. FR 2 799 955, FR 2 799 956, FR 2 799 970, and FR 2 799 971.

One drawback associated with the use of these hair care compositions lies in the fact that the cosmetic effects imparted by such compositions have a tendency to disappear, for instance at the first shampooing.

In order to obviate this drawback, consideration might be given to increasing the persistence of the polymer deposit by carrying out direct polymerization of certain monomers within the hair. For example, U.S. Pat. No. 4,344,763 describes a composition for fixing hair on the basis of a reactive aminoalkylalkoxysilane silicone and an ester titanate. Also known is the coating of the hair on the basis of a composition comprising an electrophilic cyanoacrylate monomer, for instance in French Patent Application No. FR 2 833 489. A composition of this kind allows outstandingly coated hair to be obtained which is not greasy. However, the coating obtained does not provide complete satisfaction when confronted with external agents such as washing and perspiration. Moreover, the coating obtained is sensitive to fatty substances such as sebum.

The documents WO 01/96450, GB 2 407 496 and EP 465 744 describe the use of particular reactive silicones for producing a film on the skin. The documents WO 01/96450 and GB 2 407 496 describe a formulation with one part which comprises a polysiloxane having terminal trialkoxyalkylsilyl groups, a catalyst, a solvent, and optionally an alkoxysilane and fillers. These compositions allow a film to be obtained on the skin by condensation. The document EP 465 744 describes the use of polysiloxane containing unsaturated aliphatic groups in order to produce medical devices for topical use.

The aim of the present disclosure is to develop a new system for treating hair that may provide durable fixing of the hair, while still preserving good cosmetic properties.

The present disclosure accordingly provides a composition for treating keratin fibers, comprising at least one compound X and at least one compound Y, wherein at least one of the compounds X and Y is a silicone compound, wherein when X and Y are placed in contact with each other they are able to react together via a hydrosilylation reaction, a condensation reaction or a crosslinking reaction in the presence of a peroxide; and at least one alkoxysilane comprising a single silicon atom.

The present disclosure also provides a method of treating hair, which comprises applying to the hair at least one compound X and at least one compound Y, wherein at least one of the compounds X and Y is a silicone compound, wherein when X and Y are placed in contact with each other they react together via a hydrosilylation reaction in the presence of a catalyst, a condensation reaction, or a crosslinking reaction in the presence of a peroxide; and at least one alkoxysilane comprising a single silicon atom.

The present disclosure additionally provides for the use of the combination of the compounds at least one X, at least one Y, and at least one alkoxysilane comprising a single silicon atom for treating hair, for instance for obtaining a coating which is resistant to shampooing of the hair.

Another aspect of the present disclosure relates to a kit for the treatment of keratin fibers, comprising at least two separately packaged compositions, the kit comprising at least one compound X and at least one compound Y, at least one of compounds X and Y being a silicone compound, wherein when X and Y are placed in contact with each other they react; and at least one alkoxysilane containing a single silicon atom.

The method of the present disclosure allows a coating to be obtained, in situ, that can be persistent, homogeneous and smooth and that can possess excellent adhesion to hair. Moreover it has been found, surprisingly and unexpectedly, that the hair can be shaped by the formulation of locks—that is, of cohesive individualized collectives of at least ten hairs, each bonded to the others, which are resistant to shampooing. Cohesive individualized collectives of this kind allow sophisticated hair styles to be obtained, for example, formal hair styles which are resistant to washing.

Compounds X and Y

A silicone compound is a compound comprising at least two organosiloxane units. In at least one embodiment the at least one compound X, and the at least one compound Y are both silicone compounds. The compounds X and Y may be aminated or non-aminated. They may comprise polar groups that may be chosen from: —COOH, —COO$^-$, —COO—, —OH, —NH$_2$, —NH—, —NR—, —SO$_3$H, —SO$_3^-$, —OCH$_2$CH$_2$—, —O—CH$_2$CH$_2$CH$_2$—, —O—CH$_2$CH(CH$_3$)—, —NR$_3^+$, —SH, —NO$_2$, I, Cl, Br, —CN, —PO$_4^{3-}$, —CONH—, —CONR—, —CONH$_2$, —CSNH—, —SO$_2$—, —SO—, —SO$_2$NH—, —NHCO—, —NHSO$_2$—, —NHCOO—, —OCONH—, —NHCSO— and —OCSNH—, with R representing an alkyl group.

In another embodiment at least one of the compounds X and Y is a polymer whose main chain is formed predominantly of organosiloxane units.

Some of the silicone compounds mentioned below may have both film-forming properties and adhesive properties, depending, for example, on their proportion of silicone or on whether they are used in a mixture with a specific additive. It is possible, consequently, to modify the film-forming properties or the adhesive properties of such compounds in accordance with the intended use; this is the case, for example, for the reactive elastomeric silicones known as "room temperature vulcanization" silicones.

When placed in contact with each other, the at least one compound X and the at least one compound Y react together at a temperature varying between ambient temperature and 180° C. According to at least one embodiment that at least one compound X and at least one compound Y, when placed in contact with each other, react together at ambient temperature (20±5° C.) and atmospheric pressure, for instance in the presence of a catalyst, via a hydrosilylation reaction or a condensation reaction, or a crosslinking reaction in the presence of a peroxide.

Compounds X and Y Able to React by Hydrosilylation

In one embodiment the at least one compounds X and Y react by hydrosilylation, a reaction which can be depicted in a simplified way as follows:

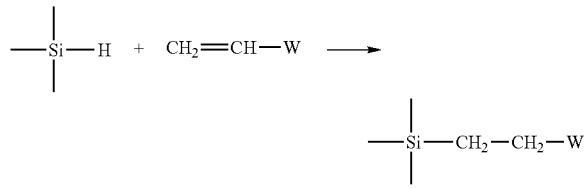

wherein:

W represents a carbon and/or silicone chain containing at least one unsaturated aliphatic group.

In this case the at least one compound X may be chosen from silicone compounds comprising at least two unsaturated aliphatic groups. By way of non-limiting example, the at least one compound X may comprise a main silicone chain whose unsaturated aliphatic groups are pendant to the main chain (side group) or are situated at the ends of the main chain of the compound (terminal group). In the remainder of the description, these specific compounds will be referred to as polyorganosiloxanes having unsaturated aliphatic groups.

In one embodiment the at least one compound X is chosen from polyorganosiloxanes comprising at least two unsaturated aliphatic groups, for example two or three vinyl or allyl groups, each bonded to a silicon atom.

According to at least one embodiment, the compound X is chosen from polyorganosiloxanes comprising siloxane units of formula:

(I)

wherein:

R is a monovalent linear or cyclic hydrocarbon group containing 1 to 30 carbon atoms, according to at least one embodiment, containing 1 to 20, for instance 1 to 10 carbon atoms, such as, for example, a short-chain alkyl radical, containing for example 1 to 10 carbon atoms, for example, a methyl radical or a phenyl group, and according to at least one embodiment is a methyl radical, wherein:

m is 1 or 2, and

R' is:

an unsaturated aliphatic hydrocarbon group containing 2 to 10, for instance 2 to 5, carbon atoms such as, for example, a vinyl group or a group —R"—CH=CHR'" wherein R" is a divalent aliphatic hydrocarbon chain containing 1 to 8 carbon atoms which is bonded to the silicon atom, and R'" is a hydrogen atom or an alkyl radical containing 1 to 4 carbon atoms, for instance a hydrogen atom; wherein the group R' may be chosen from vinyl groups, allyl groups and mixtures thereof; or an unsaturated cyclic hydrocarbon group containing 5 to 8 carbon atoms, such as, for example, a cyclohexenyl group.

According to at least one embodiment, R' is an unsaturated aliphatic hydrocarbon group, such as a vinyl group.

According to at least one embodiment the polyorganosiloxane further comprises units of formula

(II)

wherein R is a group as defined above and n is 1, 2 or 3.

According to another embodiment, the at least one compound X may be a silicone resin containing at least two ethylenic unsaturations, the resin being capable of reacting with the compound B by hydrosilylation. Possible examples include the resins of type MQ or MT which themselves carry unsaturated reactive end groups —CH=CH$_2$.

These resins are crosslinked organosiloxane polymers.

The nomenclature of silicone resins is known by the name of "MDTQ", the resin being described as a function of the different monomeric siloxane units it comprises, with each of the letters MDTQ characterizing one type of unit.

The letter M represents the monofunctional unit of formula (CH$_3$)$_3$SiO$_{1/2}$, the silicon atom being joined to a single oxygen atom in the polymer comprising this unit.

The letter D signifies a difunctional unit (CH$_3$)$_2$SiO$_{2/2}$ wherein the silicon atom is joined to two oxygen atoms.

The letter T represents a trifunctional unit of formula (CH$_3$)SiO$_{3/2}$.

In the units M, D and T defined above, at least one of the methyl groups may be substituted by a group R other than the methyl group, such as a hydrocarbon radical (for example, alkyl) having 2 to 10 carbon atoms, or a phenyl group, or else a hydroxyl group.

Finally, the letter Q signifies a tetrafunctional unit SiO$_{4/2}$ wherein the silicon atom is bonded to four hydrogen atoms which are themselves bonded to the remainder of the polymer. Possible examples of such resins include the MT silicone resins such as the poly(phenylvinylsilsesquioxanes) like those sold under the name SST-3PV1 by Gelest.

The compounds X may contain from 0.01% to 1% by weight of unsaturated aliphatic groups.

According to at least one embodiment, the at least one compound X is chosen from polyorganopolysiloxanes, for example, those comprising the siloxane units (I) and optionally (II) described above.

The at least one compound Y, according to at least one embodiment, optionally comprises at least two free Si—H groups (hydrogenosilane groups).

For example, the at least one compound Y may be chosen from organosiloxanes comprising at least one alkylhydrogenosiloxane unit of formula:

(III)

wherein:

R is a monovalent linear or cyclic hydrocarbon group containing 1 to 30 carbon atoms, such as, for example, an alkyl radical having 1 to 30 carbon atoms, such as 1 to 20 and further, for example, 1 to 10 carbon atoms, for instance a methyl radical, or a phenyl group, and p is 1 or 2. According to at least one embodiment R is a hydrocarbon group, such as methyl.

These organosiloxane compounds Y having alkylhydrogenosiloxane units may further comprise units of formula:

as defined above.

The at least one compound Y may be a silicone resin comprising at least one unit chosen from the M, D, T and Q units as defined above and comprising at least one Si—H group, such as the poly(methylhydridosilsesquioxanes) sold under the name SST-3MH1.1 by Gelest.

For instance these organosiloxane compounds Y may comprise from 0.5% to 2.5% by weight of Si—H groups.

According to at least one embodiment, the radical R is a methyl group in the formulae (I), (II) and (III) as disclosed herein.

For instance, these organosiloxanes Y may comprise terminal groups of formula $(CH_3)_3SiO_{1/2}$.

According to at least one embodiment, the organosiloxanes Y may comprise at least two alkylhydrogenosiloxane units of formula $(H_3C)(H)SiO$ and optionally comprise units $(H_3C)_2SiO$.

Organosiloxane compounds Y of this kind containing hydrogenosilane groups are described for example in document EP 0465744.

In one version the at least one compound X is chosen from organic oligomers or polymers (organic compounds are those whose main chain is not a silicone chain, for example compounds containing no silicon atoms) or from hybrid organic/silicone polymers or oligomers, the said oligomers or polymers carrying at least two reactive unsaturated aliphatic groups, and the at least one compound Y is chosen from the aforementioned hydrogenosiloxanes.

The compound X, which is organic in nature, may then be chosen from vinyl and (meth)acrylic oligomers or polymers, polyesters, polyurethanes and/or polyureas, polyethers, perfluoropolyethers, polyolefins such as polybutene and polyisobutylene, dendrimers or hyperbranched organic polymers, or mixtures thereof.

For instance the organic polymer or the organic part of the hybrid polymer may be chosen from the following polymers:

a) ethylenically unsaturated polyesters:

this is a group of polymers of polyester type having at least 2 ethylenic double bonds distributed anywhere in the main chain of the polymer. These unsaturated polyesters are obtained by polycondensation of a mixture:

of linear or branched aliphatic or cycloaliphatic carboxylic diacids comprising 3 to 50 carbon atoms, for example, 3 to 20 and further, for example, 3 to 10 carbon atoms, such as adipic acid or sebacic acid, aromatic carboxylic diacids having for instance 8 to 50 carbon atoms, such as 8 to 20 and further, for example, 8 to 14 carbon atoms, such as phthalic acids, and according to at least one embodiment, terephthalic acid, and/or carboxylic diacids obtained from dimers of ethylenically unsaturated fatty acids, such as the dimers of oleic or linoleic acids that are described in patent application EP-A-959 066 (paragraph [0021]) and are sold under the name Pripolo® by Unichema or Empol® by Henkel, all of these diacids necessarily being devoid of polymerizable ethylenic double bonds, of linear or branched aliphatic or cycloaliphatic diols comprising 2 to 50 carbon atoms, for example, 2 to 20 and further, for example, 2 to 10 carbon atoms, such as ethylene glycol, diethylene glycol, propylene glycol, 1,4-butanediol or cyclohexanedimethanol, aromatic diols having 6 to 50 carbon atoms, for example 6 to 20 and further, for example, 6 to 15 carbon atoms, such as bisphenol A and bisphenol B, and/or diol dimers obtained from the reduction of dimers of fatty acids as defined above, and at least one carboxylic diacid or their anhydride comprising at least one polymerizable ethylenic double bond and having 3 to 50 carbon atoms, for example 3 to 20, and further, for example 3 to 10 carbon atoms, such as maleic acid, fumaric acid or itaconic acid.

b) Polyesters having side and/or terminal (meth)acrylate groups:

this is a group of polymers of polyester type which are obtained by polycondensation of a mixture:

of linear or branched aliphatic or cycloaliphatic carboxylic diacids containing 3 to 50 carbon atoms, for example, 3 to 20 and further, for example, 3 to 10 carbon atoms, such as adipic acid or sebacic acid, aromatic carboxylic diacids having 8 to 50 carbon atoms, for example, 8 to 20 and further, for example 8 to 14 carbon atoms, such as phthalic acids, and according to at least one embodiment, terephthalic acid, and/or carboxylic diacids obtained from dimers of ethylenically unsaturated fatty acids, such as the dimers of oleic or linoleic acids that are described in Patent Application No. EP-A-959 066 (paragraph [0021]) and are sold under the name Pripol® by Unichema or Empol® by Henkel, all of these diacids necessarily being devoid of polymerizable ethylenic double bonds, of linear or branched aliphatic or cycloaliphatic diols comprising for example, 2 to 50 carbon atoms, such as 2 to 20 and further, for example 2 to 10 carbon atoms, such as ethylene glycol, diethylene glycol, propylene glycol, 1,4-butanediol or cyclohexanedimethanol, aromatic diols having 6 to 50 carbon atoms, for example 6 to 20 and further, for example, 6 to 15 carbon atoms, such as bisphenol A and bisphenol B, and of at least one ester of (meth)acrylic acid and a diol or polyol having 2 to 20 carbon atoms, for example 2 to 6 carbon atoms, such as 2-hydroxyethyl (meth)acrylate, 2-hydroxypropyl (meth)acrylate and glycerol methacrylate.

These polyesters are different from those described above in section a) in that the ethylenic double bonds are situated not in the main chain but on side groups or at the end of the chains. These ethylenic double bonds are those of the (meth)acrylate groups present in the polymer.

Polyesters of this kind are sold, for example, by UCB under the name Ebecryl® (Ebecryl® 450: molar mass 1600, on average 6 acrylate functions per molecule, Ebecryl® 652: molar mass 1500, on average 6 acrylate functions per molecule, Ebecryl® 800: molar mass 780, on average 4 acrylate functions per molecule, Ebecryl® 810: molar mass 1000, on average 4 acrylate functions per molecule, Ebecryl® 50000: molar mass 1500, on average 6 acrylate functions per molecule).

c) Polyurethanes and/or polyureas having (meth)acrylate groups, obtained by polycondensation:

of aliphatic, cycloaliphatic and/or aromatic diisocyanates, triisocyanates and/or polyisocyanates, for instance, having 4 to 50, for example 4 to 30, carbon atoms, such as hexamethylene diisocyanate, isophorone diisocyanate, toluene diisocyanate, diphenylmethane diisocyanate or the isocyanurates of formula:

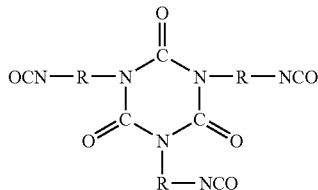

resulting from the trimerization of 3 molecules of diisocyanates OCN—R—CNO, wherein R is a linear, branched or cyclic hydrocarbon radical containing 2 to 30 carbon atoms, of polyols, for example diols, which are devoid of polymerizable ethylenic unsaturations, such as 1,4-butanediol, ethylene glycol or trimethylolpropane, and/or from polyamines, for instance diamines, which are aliphatic, cycloaliphatic and/or aromatic and have, according to at least one embodiment, 3 to 50 carbon atoms, such as ethylenediamine or hexamethylenediamine, and from at least one ester of (meth)acrylic acid and a diol or polyol having 2 to 20 carbon atoms, for example 2 to 6 carbon atoms, such as 2-hydroxyethyl (meth)acrylate, 2-hydroxypropyl (meth)acrylate and glycerol methacrylate.

Polyurethanes/polyureas of these kinds containing acrylate groups are sold for example under the name SR 368 (tris(2-hydroxyethyl) isocyanurate triacrylate) or Craynor® 435 by Cray Valley, or under the name Ebecryl® by UCB (Ebecryl® 210: molar mass 1500, 2 acrylate functions per molecule, Ebecryl® 230: molar mass 5000, 2 acrylate functions per molecule, Ebecryl® 270: molar mass 1500, 2 acrylate functions per molecule, Ebecryl® 8402: molar mass 1000, 2 acrylate functions per molecule, Ebecryl® 8804: molar mass 1300, 2 acrylate functions per molecule, Ebecryl® 220: molar mass 1000, 6 acrylate functions per molecule, Ebecryl® 2220: molar mass 1200, 6 acrylate functions per molecule, Ebecryl® 1290: molar mass 1000, 6 acrylate functions per molecule, Ebecryl® 800: molar mass 800, 6 acrylate functions per molecule).

Non-limiting mention may also be made of the water-soluble aliphatic polyurethane diacrylates sold under the names Ebecryl® 2000, Ebecryl® 2001 and Ebecryl® 2002, and of the polyurethane diacrylates in aqueous dispersion that are sold under the trade names IRR® 390, IRR® 400, IRR® 422 and IRR® 424 by UCB.

d) Polyethers having (meth)acrylate groups which are obtained by esterification, by (meth)acrylic acid, of terminal hydroxyl groups of homopolymers or copolymers of $C_{1-4}$ alkylene glycols, such as polyethylene glycol, polypropylene glycol, the copolymers of ethylene oxide and propylene oxide having, according to at least one embodiment, a weight-average molecular mass of less than 10,000, and polyethoxylated or polypropoxylated trimethylolpropane.

Polyoxyethylene di(meth)acrylates of appropriate molar mass are sold, for example, under the names SR 259, SR 344, SR 610, SR 210, SR 603 and SR 252 by Cray Valley or under the name Ebecryl® 11 by UCB. Polyethoxylated trimethylolpropane triacrylates are sold, for example, under the names SR 454, SR 498, SR 502, SR 9035 and SR 415 by Cray Valley or under the name Ebecryl® 160 by UCB. Polypropoxylated trimethylolpropane triacrylates are sold, for example, under the names SR 492 and SR 501 by Cray Valley.

e) Epoxy acrylates obtained by reacting, for example:
at least one diepoxide chosen from:
(i) bisphenol A diglycidyl ether,
(ii) a diepoxy resin resulting from the reaction of bisphenol A diglycidyl ether and epichlorohydrin,
(iii) an epoxy ester resin having α,ω-diepoxy ends, resulting from the condensation of a dicarboxylic acid having 3 to 50 carbon atoms with a stoichiometric excess of (i) and/or (ii),
(iv) an epoxy ether resin having α,ω-diepoxy ends, resulting from the condensation of the diol having 3 to 50 carbon atoms with a stoichiometric excess of (i) and/or (ii),
(v) natural or synthetic oils carrying at least 2 epoxide groups, such as epoxidized soya oil, epoxidized linseed oil and epoxidized vernonia oil,
(vi) a phenol-formaldehyde polycondensate (Novolac® resin) whose ends and/or side groups have been epoxidized,
and
at least one acid chosen from carboxylic acid and polycarboxylic acid containing at least one ethylenic double bond positioned α,β to the carboxyl group, such as (meth)acrylic acid or crotonic acid, or the esters of (meth)acrylic acid and a diol or polyol having 2 to 20 carbon atoms, for example 2 to 6 carbon atoms, such as 2-hydroxyethyl (meth)acrylate.

Polymers of this kind are sold for example under the names SR 349, SR 601, CD 541, SR 602, SR 9036, SR 348, CD 540, SR 480 and CD 9038 by Cray Valley, under the names Ebecryl® 600 and Ebecryl® 609, Ebecryl® 150, Ebecryl® 860 and Ebecryl® 3702 by UCB, and under the names Photomer® 3005 and Photomer® 3082 by Henkel.

f) Poly-$C_{1-50}$ alkyl (meth)acrylates, wherein the alkyl is linear, branched or cyclic, containing at least two functional groups having an ethylenic double bond, which are carried by the terminal and/or side hydrocarbon chains.

Copolymers of this kind are sold for example under the names IRR® 375, OTA® 480 and Ebecryl® 2047 by UCB.

g) Polyolefins such as polybutene and polyisobutylene.

h) Perfluoropolyethers having acrylate groups which are obtained by esterification, for example with (meth)acrylic acid, of perfluoropolyethers which carry terminal and/or side hydroxyl groups.

α,ω-Diol perfluoropolyethers of this kind are described, for instance, in EP-A-1057849 and are sold by Ausimont under the name Fomblin® Z DIOL.

i) Dendrimers and hyperbranched polymers which carry terminal (meth)acrylate or (meth)acrylamide groups obtained respectively by esterification or amidification of dendrimers and hyperbranched polymers having terminal hydroxyl or amino functional groups with (meth)acrylic acid.

Dendrimers (from the Greek dendron=tree) are "arborescent", in other words highly branched, polymer molecules invented by D. A. Tomalia and his team at the beginning of the 1990s (Donald A. Tomalia et al., Angewandte Chemie, Int. Engl. Ed., vol. 29, no. 2, pages 138-175). These structures are constructed around a generally polyfunctional central unit. Arrayed in chains around this central unit, in accordance with a well-defined structure, are branched chain-extension units, hence giving rise to monodisperse symmetrical macromolecules which have a well-defined chemical and stereochemical structure. Polyamidoamine dendrimers are sold for example under the name Starburst® by Dendritech.

Hyperbranched polymers are polycondensates, generally of polyester, polyamide or polyethyleneamine type, which are obtained from polyfunctional monomers, which have an arborescent structure similar to that of the dendrimers but much less regular than them (see, for example, documents WO-A-93/17060 and WO 96/12754).

Under the name Boltorn®, the company Perstorp sells hyperbranched polyesters. Hyperbranched polyethylene amines are found under the name Comburst® from the company Dendritech. Hyperbranched poly(esteramides) having hydroxyl ends are sold by the company DSM under the name Hybrane®.

These dendrimers and hyperbranched polymers esterified or amidified by acrylic and/or methacrylic acid differ from the polymers described in sections a) to h) above in the very large number of ethylenic double bonds present. This high functionality, most often greater than 5, makes them useful, for example, by allowing them to act as a "crosslinking node", in other words as a site of multiple crosslinking.

It is therefore possible to use these dendritic and hyperbranched polymers in combination with at least one of the polymers and/or oligomers a) to h) above.

Additional Reactive Compounds

In one embodiment the composition in accordance with the present disclosure may further comprise at least one additional reactive compound such as:

organic or inorganic particles comprising on their surface at least 2 unsaturated aliphatic groups, examples including silicas surface-treated with, for example, silicone compounds having vinyl groups, such as, for example, cyclotetramethyltetravinylsiloxane-treated silica;

silazane compounds such as hexamethyldisilazane.

Catalyst

According to the present disclosure, the hydrosilylation reaction takes place in the presence of a catalyst which may be present in the composition as disclosed herein, and according to at least one embodiment, the catalyst is based on platinum or on tin.

Non-limiting examples include catalysts based on platinum deposited on a silica gel support or on a charcoal powder (carbon) support, platinum chloride, platinum salts and chloroplatinic acids.

For instance chloroplatinic acids in hexahydrate or anhydrous form, which are readily dispersible in organosilicone media, can be used.

Non-limiting mention may also be made of platinum complexes such as those based on chloroplatinic acid hexahydrate and divinyltetramethyldisiloxane.

The catalyst may be present in the composition in accordance with the present disclosure in an amount ranging from 0.0001% to 20% by weight relative to the total weight of the composition comprising it.

In the composition of the present disclosure it is also possible to introduce polymerization inhibitors or retardants, and further, for example catalyst inhibitors, for the purpose of increasing the stability of the composition over time or of retarding the polymerization. Without limitation, mention may be made of cyclic polymethylvinylsiloxanes, for example tetravinyltetramethylcyclotetrasiloxane, and acetylenic alcohols, for instance volatile acetylenic alcohols, such as methylisobutynol.

The presence of ionic salts, such as sodium acetate, in the composition may influence the rate of polymerization of the compounds.

According to at least one embodiment, the at least one compounds X and Y can be chosen from silicone compounds able to react by hydrosilylation; for example, the compound X can be selected from polyorganosiloxanes containing units of formula (I) described above, and the compound Y can be selected from organosiloxanes containing alkylhydrogenosiloxane units of formula (III) described above.

According to at least one embodiment the at least one compound X is a polydimethylsiloxane having terminal vinyl groups, and the at least one compound Y is methylhydrogenosiloxane.

An example of a combination of compounds X and Y which react by hydrosilylation includes the following references provided by Dow Corning: DC 7-9800 Soft Skin Adhesive Parts A & B, and also the following mixtures A and B prepared by Dow Corning:

Mixture A:

| Ingredient (INCI name) | CAS No. | Amounts (% by wt.) | Function |
|---|---|---|---|
| Dimethyl siloxane, dimethylvinylsiloxy-terminated | 68083-19-2 | 55-95 | polymer |
| Silica silylate | 68909-20-6 | 10-40 | filler |
| 1,3-Diethenyl-1,1,3,3-tetra-methyldisiloxane complexes | 68478-92-2 | trace | catalyst |
| tetramethyldivinyldisiloxane | 2627-95-4 | 0.1-1 | polymer |

Mixture B:

| Ingredient (INCI name) | CAS No. | Amounts (% by wt.) | Function |
|---|---|---|---|
| Dimethyl siloxane, dimethylvinylsiloxy-terminated | 68083-19-2 | 55-95 | polymer |
| Silica silylate | 68909-20-6 | 10-40 | filler |
| Dimethyl, methyl-hydrogen siloxane, trimethylsiloxy-terminated | 68037-59-2 | 1-10 | polymer |

Compounds X and Y Able to React by Condensation

In another embodiment the at least one compound X and the at least one compound Y, when they are placed in contact with each other, react together by condensation, either in the presence of water (hydrolysis), by reaction of two compounds which carry alkoxysilane groups, or by so-called direct condensation, by reaction of a compound which carries at least one alkoxysilane group and a compound which carries at least one silanol group, or by reaction of two compounds which carry at least one silanol group.

When the condensation takes place in the presence of water, the water according to at least one embodiment is ambient moisture, the residual water of the keratin fibers or water provided by an external source, as for example by wetting of the hair beforehand (by means of an atomizer, for example).

In this mode of condensation reaction, the compounds X and Y, which are identical or different, may therefore be chosen from silicone compounds whose main chain comprises at least two alkoxysilane groups and/or at least two silanol (Si—OH) groups, which are side groups and/or chain-end groups.

In one embodiment the at least one compounds X and/or Y are chosen from polyorganosiloxanes comprising at least two alkoxysilane groups. An alkoxysilane group is a group comprising at least one moiety —Si—OR, R being an alkyl group containing 1 to 6 carbon atoms.

The at least one compounds X and Y may be chosen from polyorganosiloxanes comprising terminal alkoxysilane groups, for example those which comprise at least two terminal alkoxysilane groups, such as terminal trialkoxysilane groups.

The at least one compounds X and/or Y may comprise predominantly units of formula (IV):

  (IV)

wherein $R^9$ is a radical chosen from alkyl groups containing 1 to 6 carbon atoms, phenyl, and fluoroalkyl groups, and s is 0, 1, 2 or 3. According to at least one embodiment, $R^9$ is an alkyl group containing 1 to 6 carbon atoms. As the alkyl group, non-limiting mention may be made of methyl, propyl, butyl, hexyl and mixtures thereof, for example methyl or ethyl. As a fluoroalkyl group, non-limiting mention may be made of 3,3,3-trifluoropropyl.

According to at least one embodiment the at least one compounds X and Y, which are identical or different, are polyorganosiloxanes comprising units of formula (V):

  (V)

wherein $R^9$ is as defined above, and $R^9$ is for example a methyl radical, and further according to at least one embodiment, f has a viscosity at 25° C. ranging from 0.5 to 3000 Pa·s, for instance ranging from 5 to 150 Pa·s, such as a number ranging from 2 to 5000, and further, for example from 3 to 3000, and further still from 5 to 1000.

These at least one polyorganosiloxane compounds X and Y comprise at least two terminal trialkoxysilane groups per polymer molecule, said groups having the formula (VI):

  (VI)

wherein:
the radicals R represent independently a methyl, ethyl, n-propyl, isopropyl, n-butyl, sec-butyl or isobutyl group, such as a methyl or ethyl group,
$R^1$ is a methyl or ethyl group,
x is 0 or 1, according to one embodiment, x is 0; and
Z is chosen from the following: divalent hydrocarbon groups containing no ethylenic unsaturation and containing 1 to 18 carbon atoms (alkylene groups), the combinations of divalent hydrocarbon radicals and of siloxane segments of formula (IX):

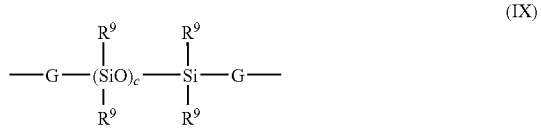  (IX)

$R^9$ being as described above, G is a divalent hydrocarbon radical containing no ethylenic unsaturation and containing 2 to 18 carbon atoms, and c is an integer of from 1 to 6.

Z and G may be chosen, for example, from alkylene groups such as methylene, ethylene, propylene, butylene, pentylene and hexylene, and arylene groups such as phenylene.

According to at least one embodiment Z is an alkylene group, such as ethylene.

These polymers may have on average at least 1.2 trialkoxysilane end groups or terminal trialkoxysilane chains per molecule, for example on average at least 1.5 trialkoxysilane end groups per molecule. These polymers may have at least 1.2 trialkoxysilane end groups per molecule, and some may comprise other types of end groups, such as end groups of formula $CH_2=CH-SiR^9_2-$ or of formula $R^6_3-Si-$, wherein $R^9$ is as defined above and each group $R^6$ is chosen independently from groups $R^9$ or vinyl. Possible examples of such end groups include trimethoxysilane, triethoxysilane, vinyldimethoxysilane and vinylmethyloxyphenylsilane groups.

Polymers of this kind are described, for example, in U.S. Pat. Nos. 3,175,993; 4,772,675; 4,871,827; 4,888,380; 4,898,910; 4,906,719; and 4,962,174, which are incorporated by reference into the present patent application.

Among possible compounds for use as at least one compound X and/or Y non-limiting mention may be made of the polymer of formula (VII):

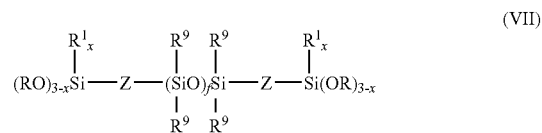  (VII)

wherein R, $R^1$, $R^9$, Z, x and f are as described above.

The compounds X and/or Y may further comprise a mixture of polymer of formula (VII) above with polymers of formula (VIII):

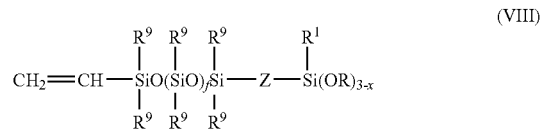  (VIII)

wherein R, $R^1$, $R^9$, Z, x and f are as described above.

When the at least one polyorganosiloxane compounds X and/or Y having at least one alkoxysilane group comprise such a mixture, the different polyorganosiloxanes are present in amounts such that the terminal organosilyl chains represent less than 40%, for example, less than 25%, by number of the terminal chains.

In at least one embodiment, the at least one polyorganosiloxane compounds X and/or Y are those of formula (VII) that were described above. Compounds X and/or Y of this kind are described, for example, in document WO 01/96450.

As indicated above, the at least one compounds X and Y may be identical or different.

In one embodiment, one of the two reactive compounds, X or Y, is of silicone type and the other is of organic type. For example, the compound X can be chosen from organic oligomers or polymers or organic/silicone hybrid oligomers or polymers, the polymers or oligomers comprising at least two alkoxysilane groups, and Y can be chosen from silicone compounds such as the polyorganosiloxanes described above. For example the organic oligomers or polymers can be chosen from vinyl and (meth)acrylic oligomers or polymers, polyesters, polyamides, polyurethanes and/or polyureas, polyethers, polyolefins, perfluoropolyethers, organic dendrimers and hyperbranched polymers, and mixtures thereof.

The organic polymers of vinyl or (meth)acrylic kind which carry alkoxysilane side groups may be obtained, for example by copolymerizing at least one vinyl or (meth)acrylic organic monomer with a (meth)acryloyloxypropyltrimethoxysilane, a vinyltrimethoxysilane, a vinyltriethoxysilane, an allyltrimethoxysilane, etc.

Non-limiting mention may be made for example of the (meth)acrylic polymers described in the document of Kusabe. M, Pitture e Vernici—European Coating; 12-B, pages 43-49, 2005, and further, for example, the polyacrylates having alkoxysilane groups that are called MAX, from Kaneka, or those described in the publication of Probster, M, Adhesion-Kleben & Dichten, 2004, 481 (1-2), pages 12-14.

The organic polymers which result from a polycondensation or from a polyaddition, such as polyesters, polyamides, polyurethanes and/or polyureas, and polyethers, and which carry alkoxysilane side and/or end groups, may result, for example, from the reaction of an oligomeric prepolymer as described above with one of the following silane coreactants which carry at least one alkoxysilane group: aminopropyltrimethoxysilane, aminopropyltriethoxysilane, aminoethylaminopropyltrimethoxysilane, glycidyloxypropyltrimethoxysilane, glycidyloxypropyltriethoxysilane, epoxycyclohexylethyltrimethoxysilane, mercaptopropyltrimethoxysilane.

Examples of polyethers and of polyisobutylenes having alkoxysilane groups are described in the publication of Kusabe, M., Pitture e Vernici—European Coating; 12-B, pages 43-49, 2005. Possible examples of polyurethanes having alkoxysilane end groups are those described in the document of Probster, M., Adhesion-Kleben & Dichten, 2004, 481 (1-2), pages 12-14 or else those described in the document of Landon, S., Pitture e Vernici vol. 73, No. 11, pages 18-24, 1997 or in the document of Huang, Mowo, Pitture e Vernici vol. 5, 2000, pages 61-67; non-limiting mention may be made, for example, of the polyurethanes having alkoxysilane groups from OSI-WITCO-GE.

As polyorganosiloxane compounds X and/or Y, non-limiting mention may be made of the resins of type MQ or MT which themselves carry alkoxysilane and/or silanol ends, such as, for example, the poly(isobutylsilsesquioxane) resins functionalized with silanol groups that are provided under the name SST-S7C41 (3 Si—OH groups) by Gelest.

Additional Reactive Compounds

The composition in accordance with the present disclosure may further comprise at least one additional reactive compound comprising at least two alkoxysilane or silanol groups.

Possible examples include at least one organic or inorganic particle comprising on its surface alkoxysilane and/or silanol groups, for example fillers surface-treated with such groups.

Catalyst

The condensation reaction may take place in the presence of a metal-based catalyst, which may be present in the composition in accordance with the present disclosure. The catalyst useful in this type of reaction, according to at least one embodiment, is a catalyst based on titanium.

Non-limiting mention may be made, for example, of the tetraalkoxytitanium-based catalysts of formula:

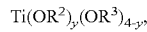

wherein $R^2$ is chosen from tertiary alkyl radicals such as tert-butyl, tert-amyl and 2,4-dimethyl-3-pentyl; $R^3$ is an alkyl radical containing 1 to 6 carbon atoms, such as a methyl, ethyl, n-propyl, isopropyl, n-butyl, sec-butyl or hexyl group; and y is a number from 3 to 4, such as from 3.4 to 4.

The catalyst may be present in the composition in accordance with the present disclosure, in an amount ranging from 0.0001% to 20% by weight, relative to the total weight of the composition.

Diluent

The composition in accordance with the present disclosure may further comprise at least one volatile silicone oil (or diluent) intended for lowering the viscosity of the composition. This oil may be chosen from short-chain linear silicones such as hexamethyldisiloxane and octamethyltrisiloxane and from cyclic silicones such as octamethylcyclotetrasiloxane and decamethylcyclopentasiloxane, and mixtures thereof.

The at least one silicone oil may be present, in an amount ranging from 5% to 95%, for example from 10% to 80%, by weight, relative to the weight of each composition.

As an example of a combination of compounds X and Y which carry alkoxysilane groups and react by condensation, mention may be made of the combination of the following mixtures A' and B', prepared by Dow Corning:

Mixture A':

| Ingredient (INCI name) | CAS No. | Amounts (% by wt.) | Function |
|---|---|---|---|
| Bis-trimethoxysiloxyethyl tetramethyldisiloxyethyl dimethicone (1) | PMN87176 | 25-45 | polymer |
| Silica silylate | 68909-20-6 | 5-20 | filler |
| Disiloxane | 107-46-0 | 30-70 | solvent |

Mixture B':

| Ingredient (INCI name) | CAS No. | Amounts (% by wt.) | Function |
|---|---|---|---|
| Disiloxane | 107-46-0 | 80-99 | solvent |
| Tetra T butyl titanate | — | 1-20 | catalyst |

It should also be noted that the identical compounds X and Y are brought together in the mixture A'.

Crosslinking in the Presence of Peroxide

In another embodiment the at least one compound X and the at least one compound Y, when they are placed in contact with each other, react together via crosslinking in the presence of peroxide. This reaction takes place, for example, by heating at a temperature greater than or equal to 50° C., such as greater than or equal to 80° C., and of up to 120° C.

In this case the at least one compounds X and Y, which are identical or different, comprise at least two —CH$_3$ side groups and/or at least two side chains which carry a —CH$_3$ group.

The at least one compounds X and Y may be silicone compounds chosen, for example, from non-volatile linear polydimethylsiloxanes of high molecular weight, having a degree of polymerization of more than 6, which have at least two —CH$_3$ side groups joined to the silicon atom and/or at least two side chains which carry a —CH$_3$ group. Non-limiting examples include the polymers described in the "Reactive Silicones" catalog of the company Gelest Inc., 2004 edition, page 6, for instance the vinylmethylsiloxane-dimethylsiloxane copolymers (also called rubbers) of molecular weights ranging from 500,000 to 900,000 and of a viscosity greater than 2,000,000 cSt.

As peroxides which can be used in the context of the present disclosure, non-limiting mention may be made of benzyl peroxide, 2,4-dichlorobenzoyl peroxide and mixtures thereof.

In at least one embodiment the hydrosilylation reaction or the condensation reaction or else the crosslinking reaction in the presence of a peroxide between the at least one compounds X and Y is accelerated by provision of heat, with the temperature of the system being raised, for example, ranging from 25° C. to 180° C. For instance, the system will react on the keratin fibers.

Generally speaking, irrespective of the type of reaction by which the at least one compounds X and Y react together, the molar percentage of X relative to the entirety of the at least one compounds X and Y, i.e. the ratio X/(X+Y)×100, may range from 5% to 95%, for example ranging from 10% to 90%, such as from 20% to 80%.

Similarly, the molar percentage of Y relative to the entirety of the compounds X and Y, i.e. the ratio Y/(X+Y)×100, may range from 5% to 95%, for example from 10% to 90%, such as from 20% to 80%.

The at least one compound X may have a weight-average molecular mass (Mw) ranging from 150 to 1,000,000, for example from 200 to 800,000, and further, for example from 200 to 250,000.

The at least one compound Y may have a weight-average molecular mass (Mw) ranging from 200 to 1,000,000, for example from 300 to 800,000, such as from 500 to 250,000.

The at least one compound X may be present in an amount ranging from 0.5% to 95% by weight, relative to the total weight of the composition, for example from 1% to 90% by weight, and further for example from 5% to 80% by weight.

The at least one compound Y may be present in an amount ranging from 0.05% to 95% by weight, relative to the total weight of the composition, for example from 0.1% to 90% by weight, and further for example from 0.2% to 80% by weight.

The ratio between the at least one compounds X and Y may be changed so as to modify the rate of reaction and hence the rate at which the film is formed, or else so as to adapt the properties of the resulting film (for example its adhesive properties) in accordance with the desired application.

For instance, the at least one compounds X and Y may be present in a molar X/Y ratio ranging from 0.05 to 20, for example from 0.1 to 10.

Alkoxysilane Comprising a Silicon Atom

The alkoxysilanes useful in the present disclosure can be chosen from those of formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

Other useful alkoxysilanes are cited, for example, in Patent Application EP 1 216 022, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST.

According to at least one embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in Patent Application EP 1 510 197.

In another embodiment, the useful alkoxysilanes may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:

3-(m-aminophenoxy)propyltrimethoxysilane, of the formula:

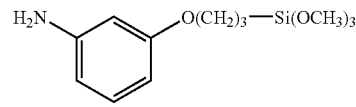

provided by GELEST, p-aminophenyltrimethoxysilane, of formula:

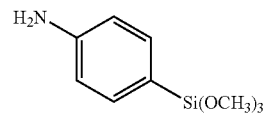

provided by GELEST, and

N-(2-aminoethylaminomethyl)phenethyltrimethoxysilane, of the formula:

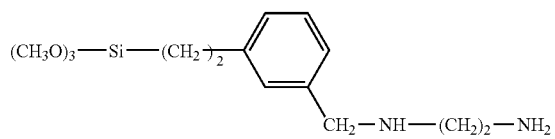

provided by GELEST.

According to at least one embodiment, the at least one organic silicon compound is N-(2-aminoethylaminomethyl)phenethyltrimethoxysilane.

The alkoxysilanes of the present disclosure may also be silanes having an aldehyde or acetal functional group, such as the triethoxysilylbutyraldehyde of formula $(CH_3CH_2O)_3Si(CH_2)_5CHO$ or the triethoxysilylunedecanol ethylene glycol acetal $(CH_3CH_2O)_3Si(CH_2)_{10}CH(OCH_2)_2$, which are provided by GELEST.

The alkoxysilanes may also be silanes containing non-primary amines, such as the bis[3-(triethoxysilyl)propyl] amine of the formula $(CH_3CH_2O)_3$—$Si(CH_2)_3NH(CH_2)_3Si(OCH_2CH_3)_3$ provided by Fluorochem, the bis[trimethoxysilylpropyl]amine of the formula $(CH_3O)_3$—$Si(CH_2)_3NH(CH_2)_3Si(OCH_3)_3$ provided by Gelest, the bis[methyldiethoxysilylpropyl]amine of the formula $(CH_3CH_2O)_2CH_3Si(CH_2)_3NH(CH_2)_3SiCH_3(OCH_2CH_3)_2$ provided by Gelest and the bis[3-trimethoxysilylpropyl]ethylenediamine of formula (CH$_3$O)$_3$Si(CH$_2$)$_3$NH(CH)$_2$NH(CH$_2$)$_3$Si(OCH$_3$)$_3$ provided by Gelest.

In another embodiment the at least one alkoxysilane is a trialkoxysilane comprising an amino substituent.

The at least one organic silicon compound present in the composition as disclosed herein may be present in a total amount ranging from 0.1% to 50% by weight, relative to the total weight of the composition, such as from 1% to 25%.

The composition of the present disclosure may contain water or at least one organic solvent, or a mixture of water and at least one organic solvent.

The at least one organic solvent may be an organic substance which is liquid at a temperature of 25° C. and at atmospheric pressure (760 mm Hg) and is capable of dissolving another substance without chemically modifying it.

The at least one organic solvent or solvents useful in the present disclosure is distinct from the at least one compounds X and Y defined above.

The at least one organic solvent can be chosen, for example, from aromatic alcohols such as benzyl alcohol; liquid fatty alcohols, for instance C10-C30 alcohols; modified or unmodified polyols such as glycerol, glycol, propylene glycol, dipropylene glycol, butylene glycol and butyl diglycol; volatile silicones such as short-chain linear silicones such as hexamethyldisiloxane and octamethyltrisiloxane, cyclic silicones such as octamethylcyclotetrasiloxane, decamethylcyclopentasiloxane and dodecamethylcyclohexasiloxane, polydimethylsiloxanes with or without modification by alkyl and/or amine and/or imine and/or fluoroalkyl and/or carboxylic and/or betaine and/or quaternary ammonium functions; liquid modified polydimethylsiloxanes; mineral, organic or vegetable oils; alkanes, such as, C5 to C10 alkanes; liquid fatty acids; and liquid fatty esters, and further, for example, the benzoates or the salicylates of liquid fatty alcohols.

The at least one organic solvent can be chosen from, for example, organic oils; silicones such as volatile silicones, amino or non-amino silicone oils or rubbers, and mixtures thereof; mineral oils; vegetable oils such as olive oil, castor oil, rapeseed oil, coconut oil, wheatgerm oil, sweet almond oil, avocado oil, macadamia oil, apricot oil, safflower oil, candlenut oil, camelina oil, tamanu oil or lemon oil, or organic compounds such as C5-C10 alkanes, acetone, methyl ethyl ketone, the esters of liquid C1-C20 acids and C1-C8 alcohols such as methyl acetate, butyl acetate, ethyl acetate and isopropyl myristate, dimethoxyethane, diethoxyethane, liquid C10-C30 fatty alcohols such as oleyl alcohol, esters of fatty alcohols or of liquid fatty acids such as C10-C30 fatty alcohol benzoates and mixtures thereof; isononyl isononanoate, isostearyl malate, pentaerythrityl tetraisostearate and tridecyl trimelate; polybutene oil; the mixture of cyclopentasiloxane (14.7% by weight)/α,γ-dihydroxypolydimethylsiloxane (85.3% by weight), or mixtures thereof.

According to at least one embodiment the at least one organic solvent is chosen from a silicone and a mixture of silicone such as liquid polydimethylsiloxanes and modified liquid polydimethylsiloxanes, the viscosity of the silicone and/or mixture of at 25° C., ranging from 0.1 cst to 1,000,000 cst, and further, for example ranging from 1 cst to 30,000 cst.

The following oils and mixtures of oils may be used, for example:

the alpha,omega-dihydroxypolydimethylsiloxane/-cyclopentadimethylsiloxane (14.7/85.3) mixture sold by Dow Corning under the name DC 1501 Fluid;

the alpha,omega-dihydroxypolydimethylsiloxane/-polydimethylsiloxane mixture sold by Dow Corning under the name DC 1503 Fluid;

the dimethicone/cyclopentadimethylsiloxane mixture sold by Dow Corning under the name DC 1411 Fluid or sold by Bayer under the name SF1214;

the cyclopentadimethylsiloxane sold by Dow Corning under the name DC245 Fluid;

and the respective mixtures of these oils.

These organic solvents may act as a diluent for the polycondensation reactions.

The at least one organic solvent and the water, when it is present, can be generally present in an amount that ranges from 0.01% to 99%, such as from 50% to 99% by weight, relative to the total weight of the composition.

As well as the organic solvent or solvents, the composition of the present disclosure may comprise water in an amount ranging from 1% to 99%, such as from 1% to 50%, relative to the total weight of the composition. According to at least one embodiment, however, the composition of the present disclosure is anhydrous, in other words containing less than 1% by weight of water, relative to the total weight of the composition.

The composition of the present disclosure may also take the form of an emulsion and/or may be encapsulated. When the composition is an emulsion it is composed, for example, of a dispersed or continuous phase, which may be water, C1-C4 aliphatic alcohols or mixtures thereof, and of an organic phase which is insoluble in water.

The composition may also further comprise fillers, which are, generally speaking, substantially colorless compounds which are solid at ambient temperature and atmospheric pressure and are insoluble in the composition, even when these ingredients are taken to a temperature greater than the ambient temperature.

By way of non-limiting example, these fillers may utilize talc; natural or synthetic mica, kaolin, colloidal calcium carbonate, which may be untreated or treated with stearic acid or With magnesium hydrogen carbonate, carbonate or stearate; hydroxyapatite, silica, such as fumed silicas and precipitated silicas, hydrophobically treated silicas, ground quartz, alumina, aluminium hydroxide, titanium dioxide, diatomaceous earth, iron oxide, carbon black, and graphite. Synthetic silicas whose surface is modified with silicone compounds in order to make them superficially hydrophobic may be used, for example. These fillers differ from one another in their surface properties, the silicone compounds used to treat the silica, and the way in which the surface treatment is carried out. Fillers of this kind allow a reduction in the viscosity of the formulation obtained from the at least one compounds X and/or Y. Moreover, resin-based reinforcing fillers may also be used. The composition can further comprise, for example, at least one filler that is chosen from silica, calcium carbonate and resin-based fillers. Possible examples include but are not limited to the treated fillers Cab-O-Sil® TS-530, Aerosil® R8200 and Wacker HDX H2000.

The composition in accordance with the present disclosure may also contain, in addition to the at least one compounds X and Y, the at least one alkoxysilane containing a single silicon atom, and, optionally, the at least one solvent, at least one adjuvant which is typically used in cosmetology and is chosen, for example, from reducing agents, fatty substances, plasticizers, softenings, antifoams, moisturizers, pigments, clays, UV filters, mineral colloids, peptizing agents, fragrances, preservatives, anionic, cationic, non-ionic or amphoteric surfactants, fixative or non-fixative polymers, proteins, vitamins, direct dyes, oxidation dyes, pearlizing agents, propellants, organic or inorganic thickeners such as benzylidene sorbitol and N-acylamino acids, oxyethylenated or non-oxyethylenated waxes, paraffins, solid $C_{10}$-$C_{30}$ fatty acids such as stearic acid and lauric acid, fatty amides or amides of solid fatty acids.

The compositions may be formulated in different forms, such as a lotion, an aerosol foam, a conditioner or a shampoo, a gel or a wax. The compositions may be contained in a pump flask or an aerosol spray. Following application to the hair, the compositions of the present disclosure may be rinsed off or left in.

When the composition is contained in an aerosol, it may comprise at least one propellant. The at least one propellant may be composed of the compressed or liquefied gases which are typically employed for preparing aerosol compositions. For instance air, carbon dioxide or compressed nitrogen or else a soluble gas such as dimethyl ether, halogenated (for example, fluorinated) or non-halogenated hydrocarbons (butane, propane, isobutane) and mixtures thereof can be used. When appropriate it will be possible to use pocket aerosols containing at least one pocket.

The method according to the present disclosure comprises applying to the keratin fibers:
at least one compound X and at least one compound Y, wherein at least one of the compounds X and Y is a silicone compound, and wherein when X and Y are placed in contact with each other they react together via
a hydrosilylation reaction,
a condensation reaction, or
a crosslinking reaction in the presence of peroxide; and
at least one alkoxysilane comprising a single silicon atom;
the at least one compound X, the at least one compound Y and the at least one alkoxysilane comprising a single silicon atom being as disclosed herein.

The at least one compound X, the at least one compound Y and the at least one alkoxysilane comprising a single silicon atom may be applied to the keratin fibers from a plurality of compositions comprising the at least one compound X, the at least one compound Y and the at least one alkoxysilane comprising a single silicon atom, alone or in a mixture, or from a single composition containing the at least one compound X, the at least one compound Y and the at least one alkoxysilane comprising a single silicon atom.

In another embodiment of the present disclosure a composition (A) comprising the at least one compound X, the at least one compound Y and the at least one alkoxysilane comprising a single silicon atom is applied to the keratin fibers.

According to another embodiment of the present disclosure a composition (B) comprising the at least one alkoxysilane comprising a single silicon atom, and a composition (C) comprising the at least one compound X and the at least one compound Y, are applied to the keratin fibers, the order in which the compositions (B) and (C) are applied being arbitrary.

In another embodiment of the present disclosure, a composition (B) comprising the at least one alkoxysilane comprising a single silicon atom, a composition (D) comprising the at least one compound X, and a composition (E) comprising the at least one compound Y are applied to the keratin fibers, the order in which the compositions (B), (D) and (E) are applied being arbitrary.

In another embodiment of the present disclosure a composition (F) comprising the at least one compound X and the at least one alkoxysilane comprising a single silicon atom, and a composition (E) comprising the at least one compound Y, are applied to the keratin fibers, the order in which the compositions (F) and (E) are applied being arbitrary.

In another embodiment of the present disclosure a composition (D) comprising the at least one compound X and a composition (G) comprising the at least one compound Y and the at least one alkoxysilane comprising a single silicon atom are applied to the keratin fibers, the order in which the compositions (D) and (G) are applied being arbitrary.

In all of the embodiments disclosed herein, the compositions described may comprise at least one organic solvent as described above.

According to at least one embodiment of the present disclosure the composition comprising the at least one alkoxysilane comprising a single silicon atom is applied before the at least one composition comprising the at least one compound X and/or the at least one compound Y.

When the at least one compounds X and Y react together by a crosslinking reaction, at least one peroxide as defined above is applied to the keratin fibers.

The at least one peroxide may be present in one or the other or in two or more of the compositions applied to the keratin fibers mentioned above, or in an additional composition, in which case the order in which the different compositions are applied to the keratin fibers is arbitrary.

In another embodiment of the present disclosure at least one catalyst as defined above is applied to the keratin fibers in order to activate the reaction between the at least one compound X and the at least one compound Y.

For example, the at least one catalyst may be present in one or the other or in two or more of the compositions applied to the keratin fibers mentioned above, or in an additional composition, in which case the order in which the different compositions are applied to the keratin fibers is arbitrary.

The catalysts which may be used include those described herein.

When at least one catalyst and/or at least one peroxide, the at least one compound X and the at least one compound Y are all applied to the keratin fibers, the at least one catalyst and/or the at least one peroxide are not stored simultaneously in the same composition. They can, in contrast, be mixed at the time of use.

In another embodiment of the present disclosure, at least one additional reactive compound as defined above is applied to the keratin fibers.

For example, the at least one additional reactive compound may be present in one or the other or in two or more of the compositions applied to the keratin fibers mentioned above, or in an additional composition, in which case the order in which the different compositions are applied to the keratin fibers is arbitrary.

The different compositions employed in the method in accordance with the present disclosure may be applied to wet or dry hair.

Rinsing and/or intermediate drying may be carried out between each application.

Each composition useful in the method in accordance with the present disclosure may further comprise at least one adjuvant chosen from various conventional cosmetic adjuvants as defined above.

Each composition useful in the methods as disclosed herein comprises a cosmetically acceptable medium which is a vehicle for the at least one compound X and/or the at least one compound Y, and is chosen such that when X and Y are placed in contact with each other on the hair they react together via hydrosilylation reaction, condensation reaction, or crosslinking reaction in the presence of peroxide.

The deposit thus formed has the benefit of having a low expected solubility. Moreover, it possesses a good affinity for the surface of the keratin fibers, thereby ensuring improved persistence of the deposit as a whole.

When the at least one compounds X and Y are applied separately, the layered deposit obtained may also be beneficial for preserving the cosmetic or optical properties of the compound that forms the upper part of the deposit.

In accordance with the same methods, it is possible to realize multiple superpositions of layers of at least one compounds X and Y, in order to attain the desired type of deposit (in terms of chemical nature, mechanical strength, thickness, appearance, feel, etc.).

The present disclosure further provides a kit for treating keratin fibers, comprising at least two separately packaged compositions, the kit comprising:

at least one compound X and at least one compound Y, wherein at least one of the compounds X and Y is a silicone compound, wherein when X and Y are brought into contact with each other they react together via a hydrosilylation reaction, a condensation reaction, or a crosslinking reaction in the presence of peroxide; and at least one alkoxysilane comprising a single silicon atom; and optionally comprising at least one organic solvent, wherein the at least one compound X, the at least one compound Y, the at least one alkoxysilane comprising a single silicon atom, and the at least one organic solvent are as disclosed herein.

In one embodiment of the present disclosure a first compartment comprises the composition (B) as defined above and a second compartment comprises the composition (C) as defined above.

In another embodiment a first compartment comprises the composition (B) as defined above, a second compartment comprises the composition (D) as defined above and a third compartment comprises the composition (E) as defined above.

In another embodiment of the present disclosure a first compartment contains the composition (F) as defined above and a second compartment contains the composition (E) as defined above.

In another embodiment a first compartment comprises the composition (D) as defined above and a second compartment comprises the composition (G) as defined above.

When the at least one compounds X and Y are able to react together by a crosslinking reaction, the collective of the compositions further comprises at least one peroxide as disclosed herein.

For example, one or the other or two or more of the compositions contained within the kit may further comprise at least one peroxide.

The kit may further comprise an additional composition comprising at least one peroxide in a cosmetically acceptable medium.

According to at least one embodiment of the present disclosure the collective of the compositions further comprises at least one catalyst as defined above; in other words, one or the other or two or more of the compositions contained in the kit may further comprise at least one catalyst, or the kit comprises an additional composition containing at least one catalyst in a cosmetically acceptable medium.

When the collective of the compositions comprises at least one catalyst and/or at least one peroxide, the at least one compound X, the at least one compound Y, the at least one catalyst and/or the at least one peroxide are not stored simultaneously in the same composition. They may, in contrast, be mixed at the time of use.

The present disclosure additionally provides for the use, for the treatment of keratin fibers, of:

at least one compound X and at least one compound Y, wherein at least one of the compounds X and Y is a silicone compound, wherein when X and Y are placed in contact with each other they react together via a hydrosilylation reaction, a condensation reaction, or a crosslinking reaction in the presence of at least one peroxide; and at least one alkoxysilane comprising a single silicon atom; and optionally at least one organic solvent, wherein the at least one compound X, the at least one compound Y, the at least one alkoxysilane comprising a single silicon atom, and the at least one organic solvent being as defined above.

Another aspect of the present disclosure provides for the use, for the persistent coating of keratin fibers, of:

at least one compound X and at least one compound Y, wherein the at least one of the compounds X and Y is a silicone compound, wherein when X and Y are placed in contact with each other they react together via a hydrosilylation reaction, a condensation reaction, or a crosslinking reaction in the presence of at least one peroxide; and at least one alkoxysilane comprising a single silicon atom; and optionally at least one organic solvent, wherein the at least one compound X, the at least one compound Y, the at least one alkoxysilane comprising a single silicon atom, and the at least one organic solvent is as disclosed herein.

The contents of the documents mentioned previously are hereby incorporated by reference into the present patent application.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the present disclosure without, however, being limiting in nature.

EXAMPLES

Example 1

In the following example, the following mixtures A' and B' prepared by Dow Corning were used:

Mixture A':

| Ingredient (INCI name) | CAS No. | Amounts (%) | Function |
|---|---|---|---|
| Bis-trimethoxysiloxyethyl tetramethyldisiloxyethyl dimethicone (1) | PMN87176 | 25-45 | polymer |
| Silica silylate | 68909-20-6 | 5-20 | filler |
| Disiloxane | 107-46-0 | 30-70 | solvent |

Mixture B':

| Ingredient (INCI name) | CAS No. | Amounts (%) | Function |
|---|---|---|---|
| Disiloxane | 107-46-0 | 80-99 | solvent |
| Tetra T butyl titanate | — | 1-20 | catalyst |

It should be noted, furthermore, that the identical compounds X and Y are combined in the mixture A'.

The following compositions were produced:

| Composition A | |
|---|---|
| Mixture A' | 50% |
| D5 | 40% |
| Aminopropyltriethoxysilane Z 6011 (Dow Corning) | 0.5% |
| Demineralized water | 9.5% |

| Composition B | |
|---|---|
| Mixture B' | 50% |
| D5 | 50% |

Compositions A and B were mixed in a weight ratio of 10/1 and then applied to short dry hair. The hair was dried in the open air for 30 minutes and then under a hood for 30 minutes. Styling effects were obtained that were resistant to a number of shampooings. The product was removed by applying D5 to the treated hair. The hair stripped of the product had a soft and cosmetic feel, for example.

Example 2

In the following composition examples, the combination of the mixtures A1 and B1 below, prepared by Dow Corning were used:

Mixture A1:

| Ingredient (INCI name) | CAS No. | Amounts (%) | Function |
|---|---|---|---|
| Dimethyl siloxane Dimethylvinylsiloxy-terminated | 68083-19-2 | 55-95 | polymer |
| Silica silylate | 68909-20-6 | 10-40 | filler |
| 1,3-diethenyl-1,1,3,3-tetramethyldisiloxane complexes | 68478-92-2 | trace | catalyst |
| Tetramethyldivinyldisiloxane | 2627-95-4 | 0.1-1 | polymer |

Mixture B1:

| Ingredient (INCI name) | CAS No. | Amounts (%) | Function |
|---|---|---|---|
| Dimethyl siloxane, dimethylvinylsiloxy-terminated | 68083-19-2 | 55-95 | polymer |
| Silica silylate | 68909-20-6 | 10-40 | filler |
| Dimethyl, methylhydrogen siloxane, trimethylsiloxy-terminated | 68037-59-2 | 1-10 | polymer |

| Composition A | |
|---|---|
| Mixture A1 | 50% |
| D5 | 40% |
| Aminopropyltriethoxysilane Z 6011 (Dow Corning) | 0.5% |
| Demineralized water | 9.5% |

| Composition B | |
|---|---|
| Mixture B1 | 50% |
| D5 | 50% |

Compositions A and B were mixed in a weight ratio of 1/1 and then applied to dry and wet hair. The wet hair was dried in the open air for 30 minutes and then under a hood for 30 minutes. Styling effects were obtained which were resistant to a number of shampooings. The product was removed by applying D5 to the treated hair. The hair stripped of the product had a soft and cosmetic feel.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07740664B2). An electronic copy of the "Sequence Listing" will also be available from the USPTO upon request and payment of the fee set forth in 37 CFR 1.19(b)(3).

What is claimed is:

1. A composition for the treatment of keratin fibers, comprising:
at least one compound X, chosen from silicone compounds comprising at least two unsaturated aliphatic groups, and at least one compound Y, wherein when X and Y are placed in contact with each other they react together via
a hydrosilylation reaction in the presence of at least one catalyst; and
at least one alkoxysilane comprising a single silicon atom.

2. The composition according to claim 1, wherein the at least one compound X is chosen from polyorganosiloxanes comprising at least two unsaturated aliphatic groups.

3. The composition according to claim 1, wherein the at least one compound X is chosen from polyorganosiloxanes comprising siloxane units of formula (I):

  (I)

wherein:
R is a monovalent linear or cyclic hydrocarbon group containing 1 to 30 carbon atoms;
m is 1 or 2; and
R' is chosen from:
unsaturated aliphatic hydrocarbon groups containing 2 to 10 carbon atoms, and
unsaturated cyclic hydrocarbon groups containing 5 to 8 carbon atoms.

4. The composition according to claim 3, wherein R' is chosen from a vinyl group and a group —R"—CH=CHR''', wherein R" is a divalent aliphatic hydrocarbon chain containing 1 to 8 carbon atoms which is bonded to the silicon atom, and R''' is a hydrogen atom or an alkyl radical containing 1 to 4 carbon atoms.

5. The composition according to claim 3, wherein the polyorganosiloxanes further comprise units of formula (II):

  (II)

wherein R is a group as defined in claim 3, and n is 1, 2 or 3.

6. A composition for the treatment of keratin fibers, comprising:
at least one compound X,
chosen from organic oligomers and polymers, and from hybrid organic/silicone oligomers and polymers, the oligomers and polymers carrying at least two reactive unsaturated aliphatic groups; and
at least one compound Y, chosen from hydrogenosiloxanes, wherein when X and Y are placed in contact with each other they react together via
a hydrosilylation reaction in the presence of at least one catalyst; and
at least one alkoxysilane comprising a single silicon atom.

7. The composition according to claim 6, wherein the at least one compound X is chosen from vinyl and (meth)acrylic oligomers and polymers, polyesters, polyurethanes, polyureas, polyethers, perfluoropolyethers, polyolefins, and organic hyperbranched polymers and dendrimers,
wherein the polymers carry at least two reactive unsaturated aliphatic groups.

8. The composition according to claim 1, wherein the at least one compound Y is chosen from polyorganosiloxanes comprising at least two free Si—H groups.

9. The composition according to claim 1, wherein the at least one compound Y is chosen from polyorganosiloxanes comprising alkylhydrogenosiloxane units of formula (III):

  (III)

wherein:
R is a monovalent linear or cyclic hydrocarbon group containing 1 to 30 carbon atoms; and
p is 1 or 2.

10. The composition according to claim 3, wherein the radical R is a methyl group.

11. The composition according to claim 8, wherein the at least one compound Y is chosen from polyorganosiloxanes comprising terminal groups of formula $CH_3SiO_{1/2}$.

12. The composition according to claim 1, further comprising at least one catalyst based on platinum or on tin.

13. The composition according to claim 12, wherein the at least one catalyst is present in an amount ranging from 0.0001% to 20% by weight, relative to the total weight of the composition.

14. A composition for the treatment of keratin fibers, comprising:
at least one compound X, and at least one compound Y, which are identical or different, are chosen from silicone compounds whose main chain comprises at least two alkoxysilane groups and/or at least two silanol (Si—OH) groups, wherein the groups are side groups and/or chain-end groups, and
wherein, when X and Y are placed in contact with each other, they react together via condensation; and
at least one alkoxysilane comprising a single silicon atom.

15. The composition according to claim 14, wherein the at least one compound X and the at least one compound Y, which are identical or different, are chosen from polyorganosiloxanes comprising at least two alkoxysilane groups.

16. The composition according to claim 14, wherein the polyorganosiloxanes predominantly comprise units of formula (IV):

  (IV)

wherein:
$R^9$ is a radical chosen from alkyl groups containing 1 to 6 carbon atoms, phenyl, and fluoroalkyl groups; and
s is 0, 1, 2 or 3.

17. The composition according to claim 16, wherein the polyorganosiloxanes comprise units of formula (V):

  (V)

wherein:
$R^9$ is a radical chosen from alkyl groups containing 1 to 6 carbon atoms, phenyl, and fluoroalkyl groups; and
f is a number ranging from 2 to 5000 such that the polymer has a viscosity at 25° C. ranging from 0.5 to 3000 Pa·s.

18. The composition according to claim 14, wherein the polyorganosiloxanes comprise at least two trialkoxysilane end groups per molecule of polymer, wherein the groups are chosen from those of formula (VI):

  (VI)

wherein:
R is chosen from methyl, ethyl, n-propyl, isopropyl, n-butyl, sec-butyl and isobutyl groups;
$R^1$ is chosen from methyl and ethyl groups;
x is 0 or 1; and
Z is chosen from divalent hydrocarbon groups containing no ethylenic unsaturation and containing 1 to 18 carbon atoms, and the combinations of divalent hydrocarbon radicals and siloxane segments of formula:

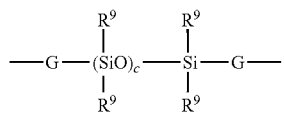

wherein:
$R^9$ is a radical chosen from alkyl groups containing 1 to 6 carbon atoms, phenyl, and fluoroalkyl groups;
G is a divalent hydrocarbon radical containing no ethylenic unsaturation and containing 2 to 18 carbon atoms; and
c is an integer from 1 to 6.

19. The composition according to claim 16, wherein the polyorganosiloxanes are chosen from the polymers of formula (VII):

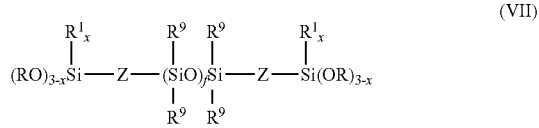 (VII)

wherein:
R is chosen from methyl, ethyl, n-propyl, isopropyl, n-butyl, sec-butyl and isobutyl groups;
$R^1$ is chosen from methyl and ethyl groups;
x is 0 or 1; and
Z is chosen from divalent hydrocarbon groups containing no ethylenic unsaturation and containing 1 to 18 carbon atoms, and the combinations of divalent hydrocarbon radicals and siloxane segments of formula:

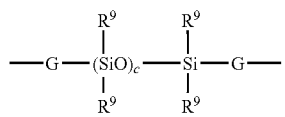

wherein:
$R^9$ is a radical chosen from alkyl groups containing 1 to 6 carbon atoms, phenyl, and fluoroalkyl groups;
G is a divalent hydrocarbon radical containing no ethylenic unsaturation and containing 2 to 18 carbon atoms; and
c is an integer from 1 to 6.

20. The composition according to claim 14, comprising at least one catalyst based on titanium.

21. The composition according to claim 20, wherein the at least one catalyst is present in an amount ranging from 0.0001% to 20% by weight, relative to the total weight of the composition.

22. A composition for the treatment of keratin fibers, comprising:
at least one compound X, chosen from silicone compounds comprising at least two unsaturated aliphatic groups, and at least one compound Y, when X and Y are placed in contact with each other, they react together via crosslinking in the presence of at least one and
at least one alkoxysilane comprising a single silicon atom.

23. The composition according to claim 1, wherein the at least one compound X has a weight-average molecular mass (Mw) ranging from 200 to 1,000,000.

24. The composition according to claim 1, wherein the at least one compound Y has a weight-average molecular mass (Mw) ranging from 200 to 1,000,000.

25. The composition according to claim 1, wherein the at least one alkoxysilane is chosen from those of formula $R_{(4-n)}SiX_n$, wherein X is an alkoxy group, R is a monovalent organic radical which contains 1 to 12 carbon atoms and optionally comprises at least one group chosen from mercapto, epoxy, acrylyl, methacrylyl, fluoro, aryl, amino and urea groups, and n is an integer from 1 to 4.

26. The composition according to claim 25, wherein the at least one alkoxysilane is chosen from 3-aminopropyltriethoxysilane and 3-mercaptopropyl-triethoxysilane.

27. The composition according to claim 1, further comprising at least one filler.

28. The composition according to claim 1, further comprising at least one organic solvent.

29. The composition according to claim 1, further comprising at least one organic silicone solvent.

30. A method of treating keratin fibers, comprising:
applying to the keratin fibers a composition comprising:
at least one compound X, chosen from silicone compounds comprising at least two unsaturated aliphatic groups, and at least one compound Y, wherein when X and Y are placed in contact with each other they react together via
a hydrosilylation reaction in the presence of at least one catalyst;
and
at least one alkoxysilane comprising a single silicon atom.

31. A multi-compartment kit comprising at least two compositions in separate compartments such that the collective of the compositions comprises:
at least one compound X and at least one compound Y, wherein at least one of the compounds X and Y is a silicone compound, wherein when X and Y are placed in contact with each other they react together via
a hydrosilylation reaction in the presence of at least one catalyst,
a condensation reaction, or
a crosslinking reaction in the presence of at least one peroxide; and
at least one alkoxysilane comprising a single silicon atom; and optionally
at least one organic solvent.

32. A method for dyeing keratin fibers comprising:
applying to the keratin fibers a cosmetic composition comprising:
at least one compound X, chosen from silicone compounds comprising at least two unsaturated aliphatic groups, and at least one compound Y, wherein when X and Y are placed in contact with each other they react together via
a hydrosilylation reaction in the presence of at least one catalyst;
and
at least one alkoxysilane comprising a single silicon atom; and optionally
at least one organic solvent.

* * * * *

UNITED STATES PATENT AND TRADEMARK OFFICE
CERTIFICATE OF CORRECTION

PATENT NO. : 7,740,664 B2  Page 1 of 1
APPLICATION NO. : 12/003125
DATED : June 22, 2010
INVENTOR(S) : Katarina Benabdillah It is certified that error appears in the above-identified patent and that said Letters Patent is hereby corrected as shown below:

Claim 22, col. 27, line 64,
"in the presence of at least one and" should read
--in the presence of at least one peroxide; and--

Signed and Sealed this

Thirty-first Day of August, 2010

David J. Kappos
*Director of the United States Patent and Trademark Office*